United States Patent
Lee et al.

(10) Patent No.: US 7,268,895 B2
(45) Date of Patent: Sep. 11, 2007

(54) INSPECTION SYSTEM AND A METHOD FOR INSPECTING A SEMICONDUCTOR WAFER

(75) Inventors: Kwang-Woon Lee, Seoul (KR);
Jang-Hyeok Lee, Suwon-si (KR);
Wook-Sung Son, Seongnam-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 223 days.

(21) Appl. No.: 11/052,698

(22) Filed: Feb. 7, 2005

(65) Prior Publication Data
US 2005/0213085 A1 Sep. 29, 2005

(30) Foreign Application Priority Data
Mar. 23, 2004 (KR) ...................... 10-2004-0019709

(51) Int. Cl.
*G01N 21/00* (2006.01)
*G01B 11/14* (2006.01)

(52) U.S. Cl. .................... 356/614; 356/620; 356/237.2

(58) Field of Classification Search ................ 356/614, 356/620, 237.1, 237.2, 237.3, 237.4, 237.5; 250/559.29, 559.3, 559.37
See application file for complete search history.

(56) References Cited

U.S. PATENT DOCUMENTS

| | | | | |
|---|---|---|---|---|
| 4,833,790 | A * | 5/1989 | Spencer et al. | 33/520 |
| 5,102,280 | A * | 4/1992 | Poduje et al. | 414/744.5 |
| 5,483,138 | A * | 1/1996 | Shmookler et al. | 318/568.16 |
| 5,690,744 | A * | 11/1997 | Landau | 118/715 |
| 5,742,393 | A * | 4/1998 | Landau et al. | 356/620 |
| 6,120,601 | A * | 9/2000 | Landau et al. | 117/98 |
| 6,195,619 | B1 * | 2/2001 | Ren | 702/155 |

FOREIGN PATENT DOCUMENTS

| | | |
|---|---|---|
| JP | 10-288517 | 10/1998 |
| JP | 11-003930 | 1/1999 |

* cited by examiner

*Primary Examiner*—Roy M. Punnoose
(74) *Attorney, Agent, or Firm*—F. Chau & Associates, LLC (57) ABSTRACT

An inspection system for inspecting a wafer and an inspection method thereof are provided. The inspection system includes a rotating means for turning and arranging a wafer to an inspection position, an angle measuring means for measuring a rotational angle used by the rotating means to rotate to the inspection position, an inspection apparatus for acquiring inspection data associated with the wafer, and a controller for determining an amending angle from the rotational angle and for amending the inspection data in accordance with the amending angle to calculate amended inspection data, wherein the amended inspection data reflects a state of the wafer on the rotating means.

18 Claims, 6 Drawing Sheets

Fig. 1

(PRIOR ART)

INSPECTION SYSTEM AND A METHOD FOR INSPECTING A SEMICONDUCTOR WAFER

CROSS-REFERENCE TO RELATED APPLICATION

This U.S. non-provisional patent application claims priority under 35 U.S.C. § 119 to Korean Patent Application 2004-19709 filed on Mar. 23, 2004, the entire contents of which are herein incorporated by reference.

TECHNICAL FIELD

The present invention relates to an inspection system and method, and more particularly, to an inspection system for testing a semiconductor wafer undergoing a semiconductor fabrication process and a method of inspecting the same.

DISCUSSION OF THE RELATED ART

To fabricate a semiconductor device, various semiconductor fabrication processes are applied to a semiconductor wafer. After performing, for example, predetermined fabrication processes, various inspection steps are carried out to determine whether the fabrication processes have been properly performed.

Typically, the steps used to inspect the wafer are performed on divided regions of the wafer. For example, the inspection can be applied to up, down, left, right, and center regions of the wafer or it can be applied to the entire wafer. Generally, an inspection system may include an inspection apparatus for performing a predetermined inspection of a wafer arranged on a chuck.

Figure 1:
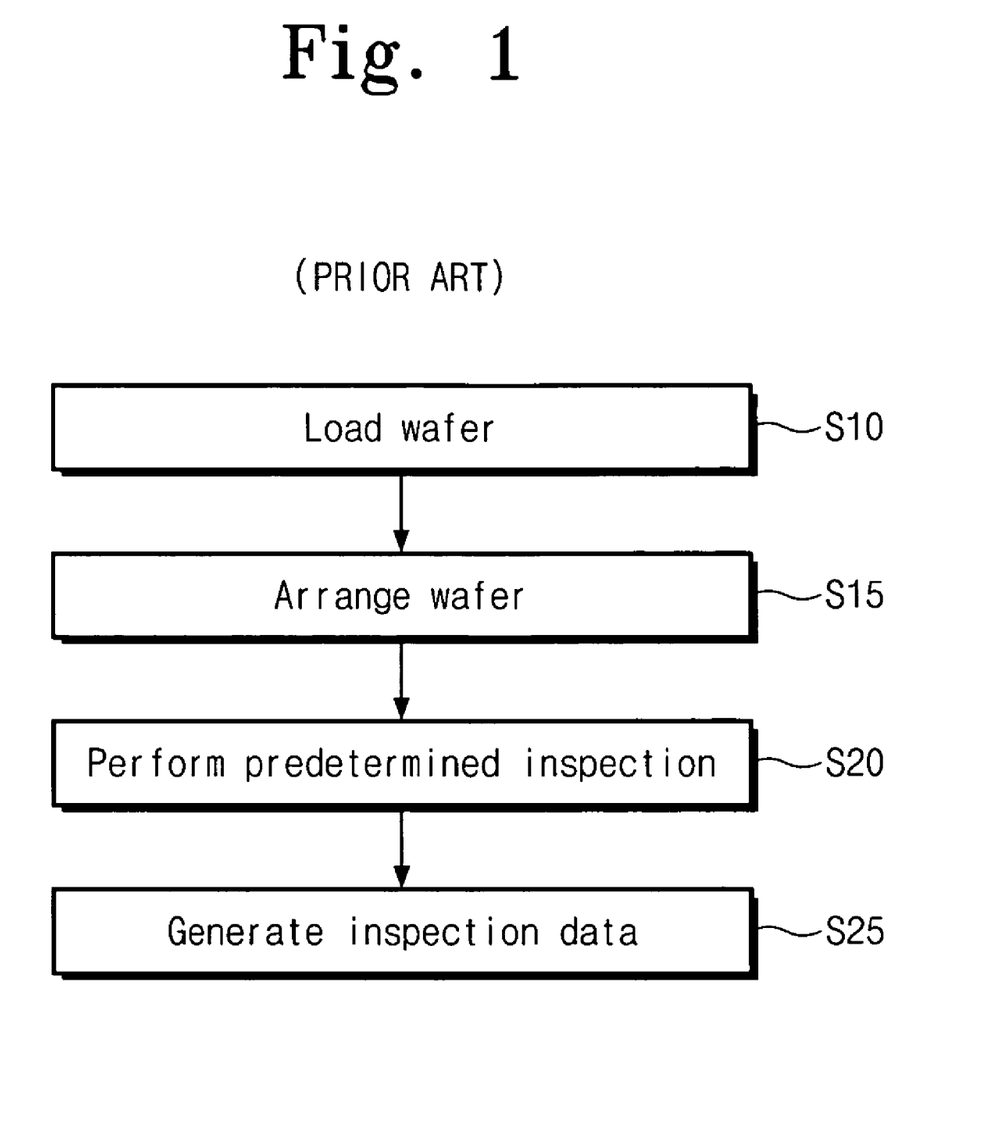
FIG. 1 is a flowchart illustrating a conventional method of inspecting a wafer.

A conventional method for inspecting a wafer using a conventional inspection system is explained below with reference to FIG. 1. Referring to FIG. 1, a wafer proceeding through a predetermined semiconductor fabrication process in a semiconductor fabrication apparatus is loaded onto a chuck of the conventional inspection system (step S10). The loaded wafer is then arranged on the chuck (step S15), and a predetermined inspection process is performed on the arranged wafer (step S20). The arrangement of the wafer enables the predetermined inspection process to be performed in divided regions of the wafer. The predetermined inspection may be related to measuring a thickness of a material layer of the wafer, its area resistance, or to measuring particle pollution. Data measured by the inspection is continuously outputted (step S25) and a process result of the inspection for the divided regions of the wafer or an amount of particle pollution can be observed by reviewing the outputted data.

It is difficult, however, to determine a state of the semiconductor fabrication apparatus, which is applying the fabrication processes to the wafer by reviewing the outputted data. For example, it is difficult to determine a relationship between the process result (or the amount of particle pollution) and the semiconductor fabrication apparatus using only conventionally outputted data.

Some semiconductor fabrication apparatuses do not need to know an arrangement of the wafer to be fabricated. For example, deposition and etching apparatuses do not need to know an arrangement of the wafer loaded thereon, especially when wafers having a notch for distinguishing up, down, left, and right directions or regions are loaded. Therefore, wafers may be loaded on the deposition or etch apparatuses in a random state (e.g., a state in which up, down, left and right directions or regions are random) and fabrication processes may be applied thereto. For example, wafers going through such processes are loaded onto the conventional inspection system, the conventional inspection system arranges them into a desirable arrangement state, and then performs an inspection.

As a result, it is difficult to determine from the data outputted by the conventional inspection system and method if there is an error with the semiconductor apparatus performing the fabrication processes or if there is an error in the outputted data. As such, a need therefore exists for an inspection system and method for testing a semiconductor wafer undergoing a semiconductor fabrication process.

SUMMARY OF THE INVENTION

According to an aspect of the present invention, an inspection system for inspecting a wafer which goes through a predetermined semiconductor process in a semiconductor apparatus is provided. The inspection system includes: a rotating means for rotating and arranging a loaded wafer to an inspection position; an angle measuring means for measuring a rotational angle of the rotating means used to turn to the inspection position; an inspection apparatus for measuring predetermined inspection data with respect to the arranged wafer; and a control device for determining an amending angle from the measured rotational angle and for amending the measured inspection data in accordance with the amending angle to calculate amended inspection data.

The angle measuring means may sense a real mark of the loaded wafer. The inspection system may further comprise a mark sensor disposed at one side of the rotating means, wherein the mark sensor senses the real mark of the loaded wafer. The control device may comprise: an arithmetic and control unit for calculating the amending angle and the amended inspection data; and a storage unit for storing at least the measured rotational angle, the measured inspection data, the amending angle and the amended inspection data. The amending angle is reverse to the measured rotational angle. More specifically, when the measured rotational angle is $360°\times n+\theta$ (where n is an integer and $\theta$ is $0 \leq |\theta| < 360°$), the amending angle may be $-\theta$. The inspection system may further comprise a display means for displaying the amended inspection data. The display means displays a data map and a map arrangement guide in which the data map includes the measured inspection data corresponding to divided regions of the wafer and a virtual mark corresponding to the real mark, wherein the map arrangement guide is disposed at one side of the data map. In this case, the data map is rotated and displayed on the display means with the virtual mark of the data map being turned as the amending angle from the map arrangement guide, and the rotated data map is the amended inspection data.

The inspection system may include: a cassette loading part for loading a cassette with the wafer; and a wafer moving means for moving the wafer between the cassette loading part and the rotating means. In this case, the amending angle may be calculated from a rotational angle measured by the angle measuring means and a rotational angle of the wafer moved from the cassette loading part to the rotating means.

According to another aspect of the present invention, a method for inspecting a wafer going through a predetermined semiconductor process in a semiconductor apparatus is provided. The method may comprise: loading the wafer on a rotating means; turning the rotating means to arrange the loaded wafer to an inspection position; measuring a rotational angle of the rotating means; acquiring inspection data associated with the arranged wafer; determining an amending angle from the measured rotational angle; and amending the inspection data in accordance with the amending angle to calculate amended inspection data.

Before loading the wafer on the rotating means, the method may further comprise: loading a cassette with the wafer on the cassette loading part at one side of the rotating means; and moving the wafer from the loaded cassette to the rotating means. In this case, the amending angle is calculated from a rotational angle measured by the rotating means and a rotational angle of the wafer moved from the cassette loading part by the rotating means. The steps of arranging the wafer loaded on the rotating means and measuring the rotational angle of the rotating means may be performed at the same time. The amending angle is reverse to the measured rotational angle. Specifically, when the measured rotational angle is 360°×n+θ (where n is an integer and θ is 0≦|θ|<360°), the amending angle may be −θ.

After calculating the amended inspection data, the inspection method further comprises displaying the amended inspection data on the display means. The display means displays a data map and a map arrangement guide in which the data map includes the measured inspection data corresponding to divided regions of the wafer and a virtual mark corresponding to the real mark, wherein the map arrangement guide is disposed at one side of the data map. In this case, the data map is rotated and displayed on the display means with the virtual mark of the data map being turned according to the amending angle from the map arrangement guide, wherein the rotated data map is the amended inspection data.

According to yet another aspect of the present invention, a system for inspecting a wafer is provided. The system comprises: an arrangement unit comprising: a rotator for rotating and arranging a wafer to an inspection position; a mark sensor for sensing a real mark of the wafer; and an angle measurer for measuring a rotational angle used by the rotator to turn to the inspection position; a inspection unit comprising: an inspection chuck for receiving the wafer; and an inspection apparatus for acquiring inspection data associated with the wafer; a cassette loading unit comprising a cassette for mounting the wafer; a return unit comprising: a wafer mover for moving the wafer among the arrangement unit, cassette loading unit, and inspection unit; and a controller for determining an amending angle from the rotational angle and for amending the inspection data in accordance with the amending angle to calculate amended inspection data, wherein the controller comprises: an arithmetic and control unit for calculating the amending angle and the amended inspection data; and a storage unit for storing the rotational angle, inspection data, amending angle and amended inspection data.

BRIEF DESCRIPTION OF THE DRAWINGS

The above and other features of the present invention will become more apparent by describing in detail exemplary embodiments thereof with reference to the attached drawings, in which.

DETAILED DESCRIPTION OF EXEMPLARY EMBODIMENTS

Figure 2:
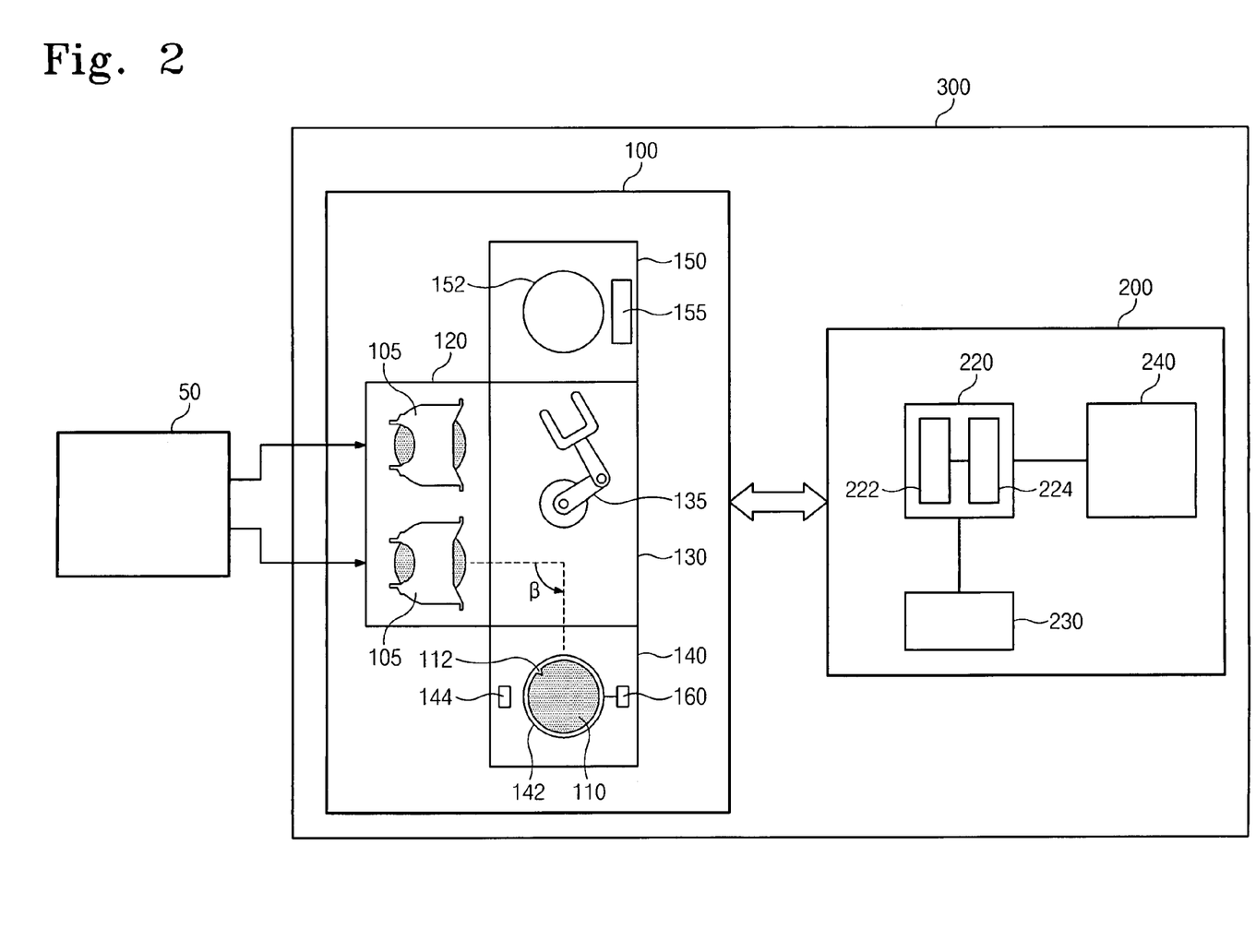
FIG. 2 illustrates an inspection system for inspecting a wafer in accordance with an exemplary embodiment of the present invention.
Figure 3:
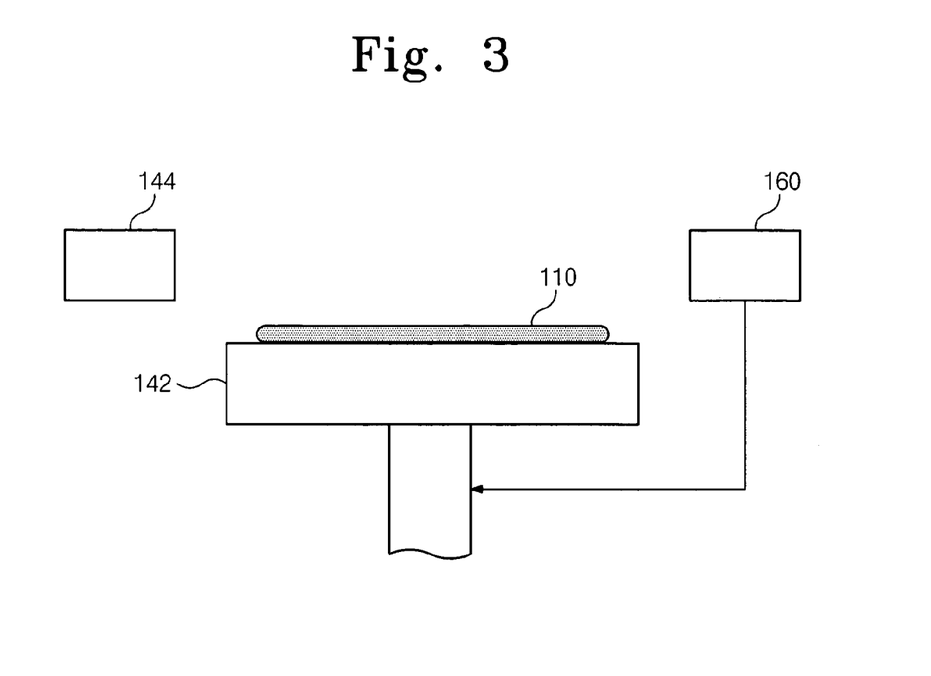
FIG. 3 illustrates an arrangement unit of FIG. 2.

FIG. 2 illustrates an inspection system 300 for inspecting a wafer in accordance with an exemplary embodiment of the present invention. FIG. 3 illustrates an arrangement unit 140 of the inspection system 300.

Referring to FIGS. 2 and 3, the inspection system 300 may include an inspection unit 100 and an operator interface 200. The inspection unit 100 and the operator interface 200 may exchange data signals via network interfaces such as RS232C interfaces through a data bus.

The inspection unit 100 may include a cassette loading part 120, a return unit 130, the arrangement unit 140 and an inspection device 150. A cassette 105 mounted with a plurality of wafers 110 is loaded onto the cassette loading part 120. The wafer or wafers 110 mounted in the cassette 105 go through a preset semiconductor fabrication process, for example, in a semiconductor fabrication apparatus 50. The semiconductor fabrication apparatus 50 may be an apparatus that does not have to arrange the wafers 110. For example, the semiconductor fabrication apparatus 50 may be a deposition apparatus, an etch apparatus, an ion implantation apparatus or a cleaning apparatus. The semiconductor fabrication apparatus 50 may also be an apparatus that arranges wafers therein such as a photolithography apparatus. The cassette loading part 120 may include a plurality of cassette ports in order to improve throughput.

The wafer 110 may include a real mark 112 for distinguishing up, down, left, and right directions or regions of the wafer 110. As shown in FIG. 2, the real mark 112 may be a notch for indicating a specific direction formed at an edge of the wafer 110. The real mark 112 may also be a flat zone formed at a portion of a flat edge of the wafer 110. In addition, the real mark 112 may be a specific pattern that is formed at a predetermined region on an upper surface of the wafer 110.

The return unit 130 is disposed at one side of the cassette loading part 120. The arrangement unit 140 is disposed at one side of the return unit 130. The inspection device 150 may be disposed at another side of the return unit 130. A wafer moving means 135 is located in the return unit 130. The wafer moving means 135 may be a robot arm. The wafer moving means 135 moves the wafer 110 in the cassette loading part 120, the arrangement unit 140, and the inspection device 150.

The arrangement unit 140, which is where the wafer 110 is arranged, includes a rotating means 142 with the wafer 110 loaded thereon. The rotating means 142 rotates the wafer 110 from a loaded position to an inspection position. The rotating means 142 may be, for example, an arrangement chuck. A mark sensor 144 for sensing the real mark 112 of the wafer 110 may be disposed at one side of the rotating means 142. The rotating means 142 may rotate the loaded wafer 110 to the inspection position by means of the mark sensor 144.

An angle measuring means 160 is disposed at another side of the rotating means 142. The angle measuring means 160 will be explained with reference to FIG. 4.

Figure 4:
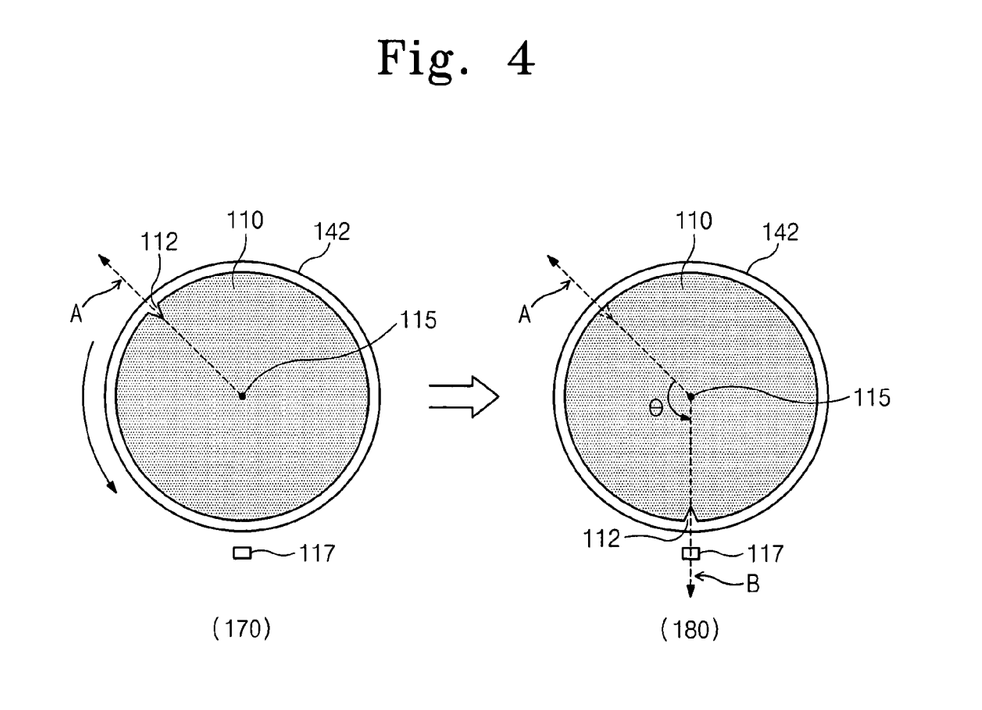
FIG. 4 illustrates a rotational angle measuring apparatus of FIG. 2.

FIG. 4 illustrates the angle measuring means 160. In FIG. 4, reference numbers "170" and "180" represent when the wafer 110 is loaded and when the wafer 110 is arranged at an inspection position, respectively.

Referring now to FIGS. 2, 3 and 4, the angle measuring means 160 measures a rotational angle of the rotating means 142, which is used to arrange the wafer 110 from the loaded position to the inspection position. For example, the wafer 110 is first loaded on the rotating means 142 and the rotating means 142 then turns the loaded wafer 110 and aligns it to the inspection position using the mark sensor 144 for sensing the real mark 112 of the wafer 110. In this case, the angle measuring means 160 measures the rotational angle of the rotating means 142.

The real mark 112 of the loaded wafer 110 may head in an A-direction as shown in FIG. 4. The A-direction is a direction heading out from a center point 115 of the wafer 110. A wafer align guide 117 is placed in a B-direction also heading out from the center point 115. The B-direction is an arrangement direction of the real mark 112 required by the inspection system 300. The A-direction is disposed in a random direction separate from the B-direction. The real mark 112 of the wafer 110 aligned by the rotating means 142 is aligned in the B-direction. Thus, the aligned real mark 112 of the wafer 110 and the wafer alignment guide 117 are disposed in the B-direction. In this case, an angle θ turning from the A-direction to the B-direction is included in the rotational angle measured by the angle measuring means 160. The rotational angle measured by the angle measuring means 160 may be 360°×n+θ. In this case, n is an integer and θ is 0≦|θ|<360°.

The rotating means 142 may turn clockwise or counterclockwise. In addition, the rotating means 142 alternate between turning clockwise and counterclockwise to align the wafer 110. In this case, the angle measuring means 160 receives one of the right or left directions as a positive value and the other as a negative value. Then, the angle measuring means 160 may measure the rotational angle of the rotating means 142. The angle measuring means 160 may further perform a sensing function for sensing the real mark 112. In this case, the mark sensor 144 is not needed.

Referring again to FIGS. 2 and 3, an inspection chuck 152 may be disposed on the inspection device 150 and the aligned wafer 110 may be moved to the inspection chuck 152 by the wafer moving means 135. An inspection apparatus 155 is also disposed at one side of the inspection chuck 152. The inspection apparatus 155 may apply a predetermined inspection process to the wafer 110 loaded on the chuck 152. For example, the inspection apparatus 155 may measure a thickness or a surface resistance of the wafer. Meanwhile, the inspection apparatus 155 may measure a defect in the wafer such as particle pollution or a scratch. In addition, the inspection apparatus 155 may measure a doped concentration of ions on a region implanted with impurity ions. Moreover, the inspection apparatus 155 may perform a variety of inspections known to those of skill in the art for fabricating a semiconductor device.

The operator interface 200 includes a control device 220, an input means 230 and a display means 240. The input device 230 may be a keyboard or a mouse. The operator interface 200 may be a computer system connected through a network and separate from the inspection unit 100. The operator interface 200 may also be attached to the inspection unit 100 to form a stand alone system.

The control device 220 receives a rotational angle measured by the rotational measuring means 160 and inspection data measured by the inspection apparatus 155. The control device 220 calculates an amending angle from the measured rotational angle and amends the measured inspection data as the amending angle to calculate the inspection data. The amended inspection data reflects a state of loaded wafer 110. Therefore, a state of the semiconductor apparatus 50 applying a predetermined semiconductor process to the wafer 110 can be determined from the amended inspection data.

The control device 220 may further include an arithmetic and control unit 222 and a storage unit 224. The arithmetic and control unit 222 calculates the amending angle and the amended inspection data. The storage unit 224 may store at least the measured rotational angle, the measured inspection data, the amending angle and the amended inspection data. The control device 220 may display the amending angle and the amended inspection data on the display means 240. The control device 220 and the display means 240 will be described in more detail with reference to FIG. 5.

Figure 5:
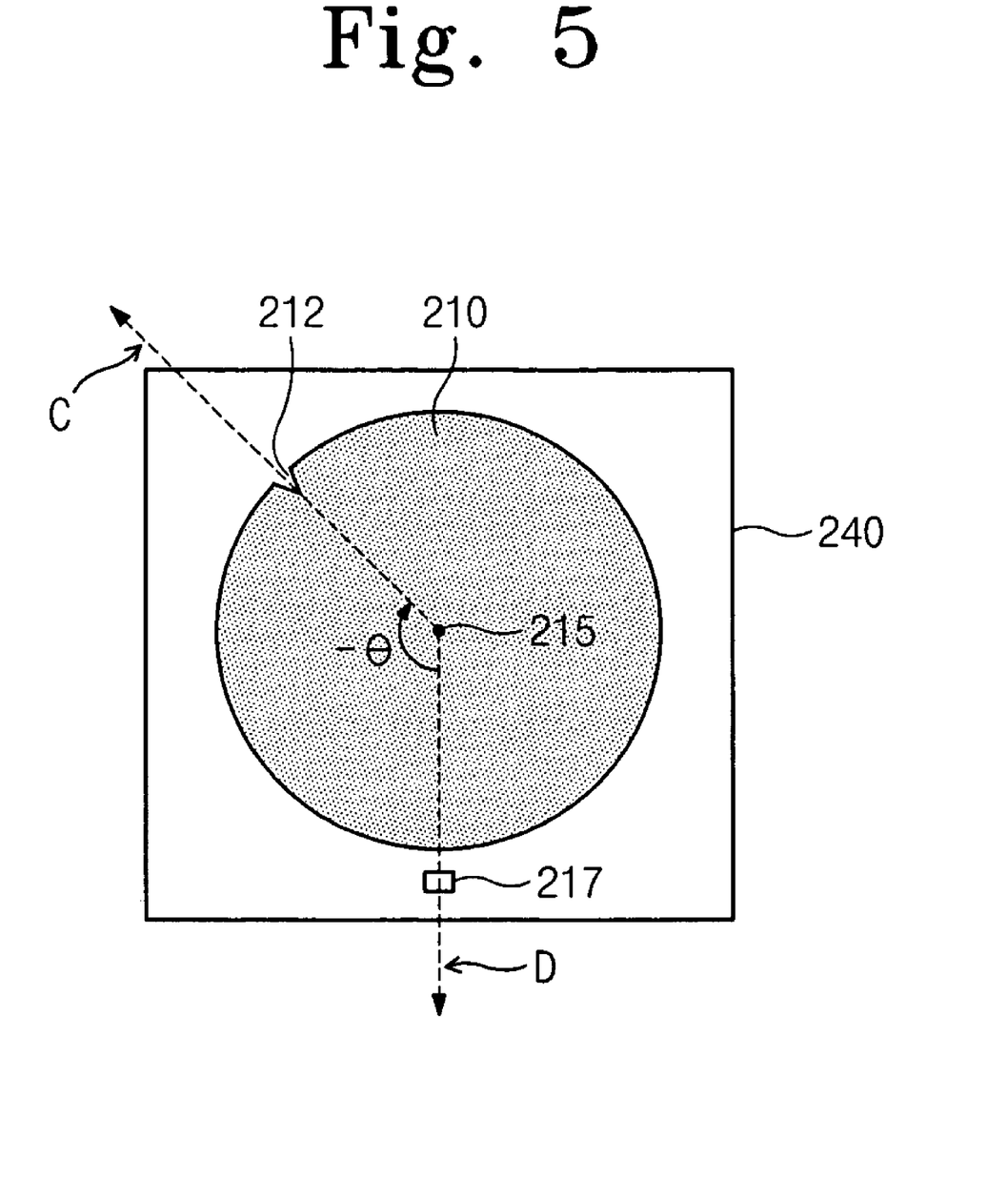
FIG. 5 illustrates a display means of FIG. 2.

FIG. 5 illustrates the display means 240. Referring now to FIGS. 2 through 5, the display means 240 is an output apparatus that displays the amended inspection data, and may be an image output apparatus such as a computer monitor. The display means 240 may also be a printer for printing the amended inspection data.

A data map 210 is displayed on the display means 240. The data map 210 includes regions corresponding to divided regions of the wafer 110. The inspection data measured by the inspection apparatus 155 associated with each divided region of the wafer 110 is displayed on the data map 210. The data map 210 includes a virtual mark 212 corresponding to the real mark 112 of the wafer 110. A map arrangement guide 217 is displayed on one side of the data map 210. The map arrangement guide 217 is used for arranging the data map 210. The display means 240 displays the data map 210 and the map arrangement guide 217. The map arrangement guide 217 corresponds to the wafer arrangement guide 117. The map arrangement guide 217 may be displayed on a lower portion of a screen of the display means 240.

The data map 210 is turned according to the amending angle about a center point 215 thereof and is displayed on the display means 240. Specifically, a C-direction heading for the virtual mark 212 from the center point 215 of the data map 210 is turned according to the amending angle from a D-direction heading for the map arrangement guide 217 from the center point 215. In other words, the data map 210 is turned according to the amending angle corresponding to the amended inspection data.

The amending angle may be reverse to the turning direction of the rotating means 142. If, for example, the rotational angle measured by the angle measuring means 160 is 120°, the amending angle may be −120°. More specifically, when the rotational means measured by the angle measuring means 160 is 360°×n+θ (where n is an integer and θ is 0≦|θ|<360°), the amending angle may be −θ.

The amending angle may further include information related to a relationship of a position between the cassette loading part 120 and the rotating means 142. More specifically, the wafer 110 may rotate an angle of β while moving from the cassette loading part 120 to the rotating means 142 as illustrated in FIG. 2. This is because the wafer 110 is moved as it is fixed to the wafer moving means 135. Therefore, if the amending angle includes information regarding the angle β, the amended inspection data may reflect the state of the wafer 110 when it is first loaded on the inspection system 300 (e.g., the state of the wafer 110 loaded on the cassette loading part 120). In this case, the amending angle is reverse to a summation of the rotational angle measured by the angle measuring means 160 and the angle β. More specifically, if the rotational angle measured by the angle measuring means 160 is 360°×n+θ (where n is an integer and θ is 0≦|θ|<360°), and the wafer 110 is turned to the angle β while moving from the cassette loading part 120 to the rotating means 142, the amending angle may be −(θ+β). The information regarding the angle β may then be inputted to the control device 220 by an input means of the operator interface 200.

Figure 6:
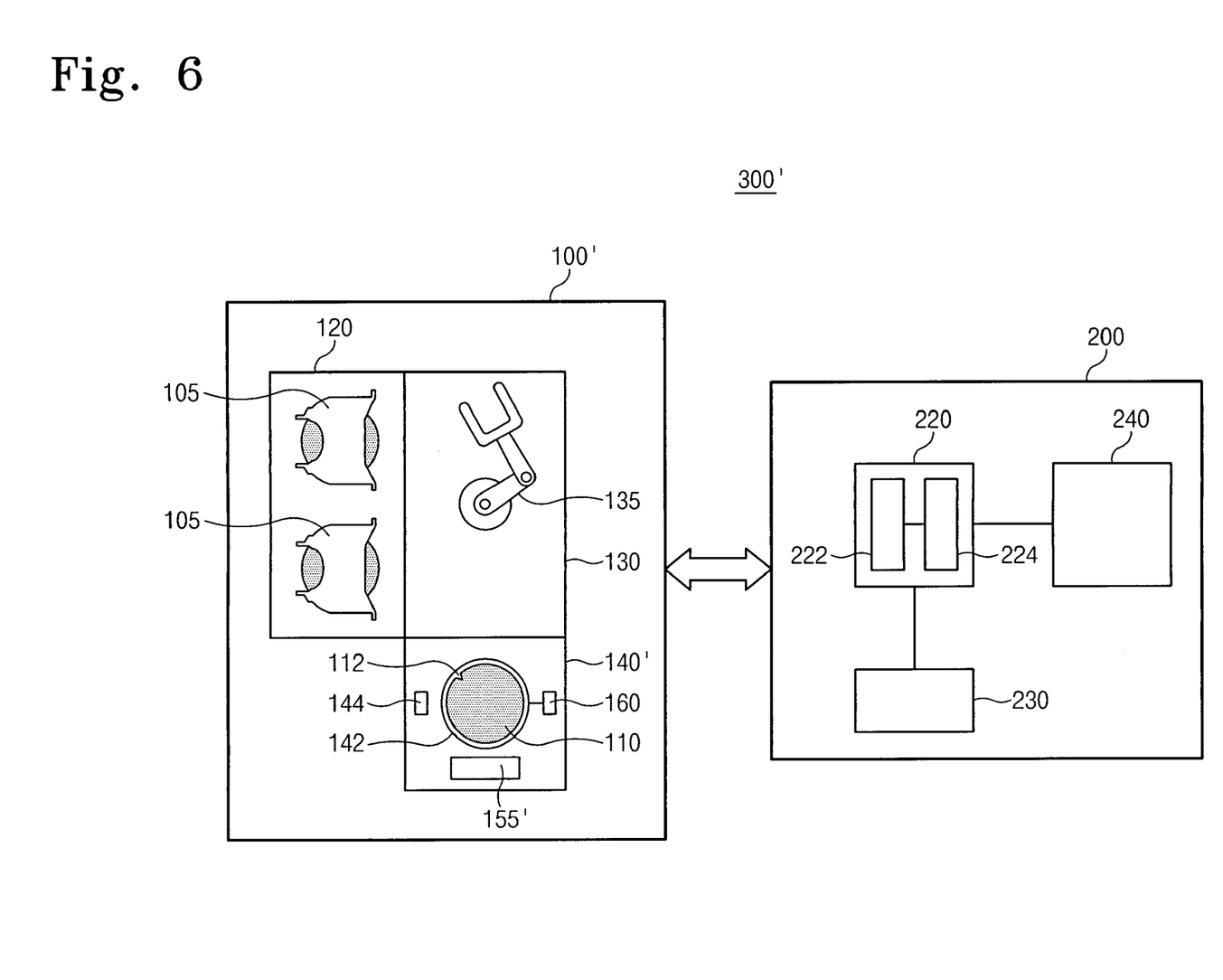
FIG. 6 illustrates an inspection system in accordance with another exemplary embodiment of the present invention.

FIG. 6 is an inspection system in accordance with another exemplary embodiment of the present invention. The elements in FIG. 6 having the same reference numerals as those in FIG. 2 perform the same or similar functions and will not be described hereinafter.

Referring to FIG. 6, the inspection system 300' includes an inspection unit 100' and an operator interface 200. The inspection unit 100' and the operator interface 200 may exchange various data signals by network connections or via data buses.

The inspection unit 100' includes a cassette loading part 120, a return unit 130 and an arrangement unit 140'. A rotating means 142, an angle measuring means 160 and an inspection apparatus 155' are disposed in the arrangement unit 140'. The inspection apparatus 155' performs an inspection process. The inspection apparatus 155' may perform the same function as the inspection apparatus 155 of FIG. 2.

As shown in FIG. 6, the inspection system 300' includes an inspection apparatus 155' at one side of the rotating means 142 and thus does not use the inspection device 150 of FIG. 2, thereby reducing production cost of the inspection system 300'. In addition, the inspection system 300' reduces a moving path of the wafer 110 to reduce inspection time, thereby improving productivity.

Figure 7:
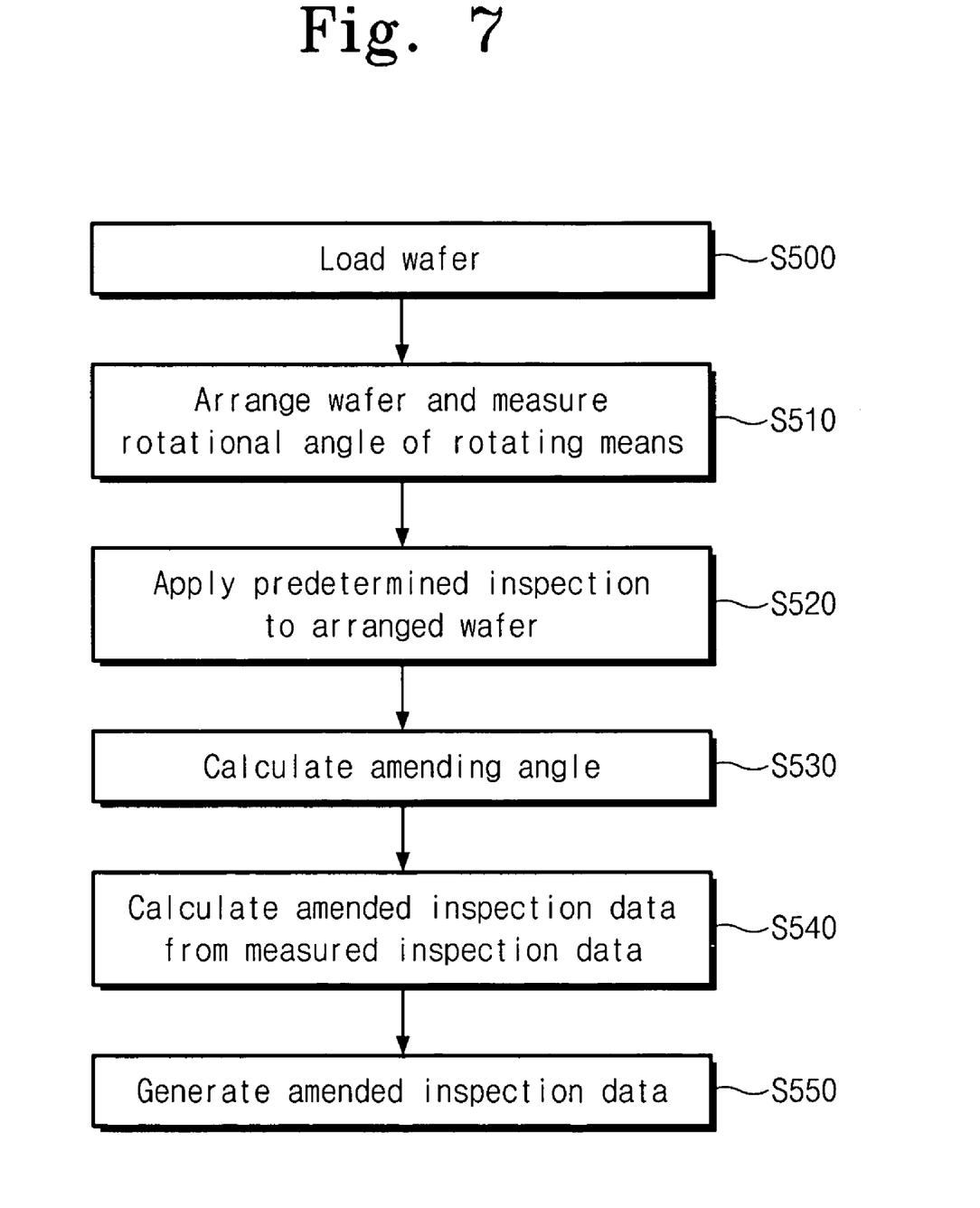
FIG. 7 is a flowchart illustrating a method of inspecting a wafer in accordance with yet another exemplary embodiment of the present invention.

A method for inspecting a wafer going through a semiconductor fabrication process in a semiconductor apparatus will now be described with reference to FIG. 7. More particularly, FIG. 7 is a flowchart illustrating a method of inspecting a wafer according to yet another exemplary embodiment of the present invention.

Referring now to FIGS. 2 through 7, a wafer 110 going through a semiconductor fabrication process in a semiconductor apparatus 50 is loaded onto an inspection system 300 (step S500). A cassette 105 mounted with wafers 110 is loaded onto the cassette loading part 120. The wafer moving means 135 loads a selected wafer 110 in the cassette 105 onto the rotating means 142.

The rotating means 142 turns the loaded wafer 110 to arrange it in an inspection position, and a rotational angle of the rotating means 142 is measured (step S510). The rotating means 142 arranges the real mark 112 of the loaded wafer 110 on the wafer arrangement guide 117 using an operation for sensing the real mark 112 of the loaded wafer 110 by the mark sensor 144. The rotating means 142 aligns the real mark 112 of the loaded wafer 110 with the wafer arrangement guide 117. In this case, the angle measuring means 160 measures the rotational angle of the rotating means 142. When the mark sensor 144 is omitted, the angle measuring means 160 may perform the operations of sensing the real mark 112 and measuring the rotational angle of the rotating means 142. The measured rotational angle is transmitted to a control device 220 through a network or data buses.

A predetermined inspection is then applied to the arranged wafer 110 (step S520). The arranged wafer 110 is moved to an inspection chuck 152 by the wafer moving means 135. The inspection apparatus 155 inspects the arranged wafer 110. If the arranged wafer 110 is disposed on the rotating means 142, the predetermined inspection is performed by the inspection apparatus 155'. The predetermined inspection may be related to measuring a thickness or surface resistance of a material layer of the wafer, a concentration of doped impurities, or defects on divided regions of wafer 110. The measured inspection data is then transmitted to the control device 220 through a network or data buses.

The control device 220 calculates an amending angle from a rotational angle measured by the angle measuring means 160 (step S530). The amending angle may be calculated using the method discussed with reference to FIGS. 2 through 5. For example, the amending angle may be reverse to the rotational angle measured by the angle measuring means 160. More specifically, when the measured rotational angle is 360°×n+θ (where n is an integer and θ is 0≦|θ|<360°), the amending angle may be −θ. Moreover, the amending angle may include information regarding a rotational angle β that rotates while the wafer 110 is moved from the cassette loading part 120 to the rotating means 142. Thus, the amending angle may be reverse to a total of the rotational angle measured by the angle measuring means 160 and the angle β. More specifically, when the rotational angle measured by the angle measuring means 160 is 360°×n+θ (where n is an integer and θ is 0≦|θ|<360°) and the wafer 110 is rotated as the angle β while the wafer is moved from the cassette loading part 120 to the rotating means 142, the amending angle may be −(θ+β). It is to be understood by one of ordinary skill in the art that the step of calculating the amending angle (step S530) may be carried out along with the step of inspecting the wafer (step S520). The two steps S520 and S530 may also be performed sequentially.

Amended inspection data is then calculated from the measured inspection data (step S540). In doing so, the control device 220 receives and amends the measured inspection data to calculate the amended inspection data. The amended inspection data reflects a state of the wafer 110 loaded onto the rotating means 142 or the inspection system 300.

The amended inspection data is then outputted (step S550). In particular, the control device 220 displays the amended inspection data on the display means 240 and the amended inspection data is shown on the display means 240 as a rotated data map 210. The virtual mark 212 of the rotated data map 210 is rotated according to the amending angle from the map arrangement guide 217. The amended inspection data may be outputted as an image or printed.

In the above described inspection systems and methods, the amended inspection data reflects a state of the wafer loaded on the inspection system, as is, when the wafer goes through a semiconductor fabrication process in the semiconductor apparatus. Therefore, even if the wafer is loaded on the semiconductor apparatus in a non-arranged state, a state of the semiconductor apparatus can be determined by the amended inspection data.

As a result, when the amended inspection data has an error, the state of the semiconductor apparatus is quickly acquired and treated as an error related to the semiconductor apparatus. Therefore, the productivity of semiconductor products fabricated using the inspection systems and methods of the present invention can be improved. In addition, the step of arranging a wafer on a chuck can be omitted before performing a semiconductor fabrication processes using a semiconductor apparatus capable of fabricating unarranged wafers. Thus, a processing time can also be reduced thereby improving a productivity of the semiconductor fabrication apparatus and products resulting therefrom.

According to exemplary embodiments of the present invention, a rotational angle of a rotating means is measured to arrange a loaded wafer in an inspection position using an angle measuring means. Therefore, even if the non-arranged wafers are loaded on a semiconductor apparatus for performing a predetermined semiconductor fabrication process, the state of the semiconductor apparatus can be determined by the amended inspection data. As a result, if there is an error in the amended inspection data, the semiconductor apparatus can be corrected to improve its productivity.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An inspection system for inspecting a wafer, comprising:
   a rotating means for rotating and arranging a wafer to an inspection position;
   an angle measuring means for measuring a rotational angle use by the rotating means to turn to the inspection position;
   an inspection apparatus for acquiring inspection data associated with the wafer; and
   a control device for determining an amending angle from the rotational angle and for amending the inspection data in accordance with the amending angle to calculate amended inspection data,
   wherein the angle measuring means senses a real mark of the wafer.

2. The system of claim 1, wherein the control device comprises:
   an arithmetic and control unit for calculating the amending angle and the amended inspection data; and
   a storage unit for storing the rotational angle, inspection data, amending angle and amended inspection data.

3. The system of claim 1, wherein the amending angle is reverse to the rotational angle.

4. The system of claim 3, wherein when the rotational angle is 360°×n+θ (where n is an integer and θ is 0≦|θ|<360°), the amending angle is −θ.

5. The system of claim 1, further comprising:
   a display means for displaying the amended inspection data.

6. The system of claim 5, wherein the display means displays a data map and a map arrangement guide in which the data map includes the inspection data corresponding to divided regions of the wafer and a virtual mark corresponding to the real mark, wherein the map arrangement guide is disposed at a first side of the (data map, and
   wherein the data map is rotated and displayed on the display means with the virtual mark turned according to the amending angle from the map arrangement guide, and
   wherein the rotated data map is the amended inspection data.

7. The system of claim 1, further comprising:
   a cassette loading unit for loading a cassette with the wafer; and
   a wafer moving means for moving the wafer between the cassette loading unit and the rotating means,
   wherein the amending angle is calculated from the rotational angle measured by the angle measuring means and a rotational angle of the wafer moved from the cassette loading unit to the rotating means.

8. The method of claim 1, wherein the wafer is undergoing a semiconductor fabrication process in a semiconductor apparatus.

9. The method of claim 8, wherein the semiconductor fabrication apparatus is one of a deposition, etch, ion implantation, cleaning, and photolithography apparatus.

10. An inspection system for inspecting a wafer, comprising:
    a rotating means for rotating and arranging a wafer to an inspection position;
    an angle measuring means for measuring a rotational angle used by the rotating means to turn to the inspection position;
    an inspection apparatus for acquiring inspection data associated with the wafer;
    a control device for determining an amending angle from the rotational angle and for amending the inspection data in accordance with the amending angle to calculate amended inspection data; and
    a mark sensor disposed at a first side of the rotating means, wherein the mark sensor senses a real mark of the wafer.

11. A method for inspecting a wafer comprising:
    loading the wafer on a rotating means;
    turning the rotating means to arrange the wafer to an inspection position;
    measuring a rotational angle of the rotating means;
    acquiring inspection data associated with the wafer;
    calculating an amending angle from the rotational angle;
    amending the inspection data in accordance with the amending angle to calculate amended inspection data; and
    displaying the amended inspection data on a display means after calculating the amended inspection data,
    wherein the display means displays a data map.

12. The method of claim 11, further comprising:
    loading a cassette with the wafer on a cassette loading unit at a first side of the rotating means; and
    moving the wafer from the cassette to the rotating means,
    wherein the amending angle is calculated from the rotational angle measured by the rotating means and a rotational angle of the wafer moved from the cassette loading unit by the rotating means, before loading the wafer on the rotating means.

13. The method of claim 11, wherein the steps of arranging the wafer on the rotating means and measuring the rotational angle of the rotating means are performed at the same time.

14. The method of claim 11, wherein the amending angle is reverse to the rotational angle.

15. The method of claim 14, wherein when the rotational angle measured by the rotating means is 360°×n+θ (where n is an integer and θ is 0≦|θ|<360°),the amending angle is −θ.

16. The method of claim 11, wherein the display means displays the data map and a map arrangement guide in which the data map includes the inspection data corresponding to divided regions of the wafer and a virtual mark corresponding to a real mark of the wafer, wherein the map arrangement guide is disposed at a first side of the data map, and wherein the data map is rotated and displayed on the display means with the virtual mark turned according to the amending angle from the map arrangement guide, and wherein the rotated data map is the amended inspection data.

17. A system for inspecting a wafer, comprising:

an arrangement unit comprising: a rotator for rotating and arranging a wafer to an inspection position; a mark sensor for sensing a real mark of the wafer; and an angle measurer for measuring a rotational angle used by the rotator to turn to the inspection position;

a inspection unit comprising: an inspection chuck for receiving the wafer; and an inspection apparatus for acquiring inspection data associated with the wafer;

a cassette loading unit comprising a cassette for mounting the wafer;

a return unit comprising: a wafer mover for moving the wafer among the arrangement unit, cassette loading unit, and inspection unit; and a controller for determining an amending angle from the rotational angle and for amending the inspection data in accordance with the amending angle to calculate amended inspection data, wherein the controller comprises: an arithmetic and control unit for calculating the amending angle and the amended inspection data; and a storage unit for storing the rotational angle, inspection data, amending angle and amended inspection data.

18. The system of claim 17, wherein when the rotational angle measured by the rotator is $360°\times n+\theta$ (where n is an integer and $\theta$ is $0\leq|\theta|<360°$) and the amending angle is $-\theta$.

* * * * *